US012806426B2

(12) United States Patent
Brandt et al.

(10) Patent No.: US 12,806,426 B2
(45) Date of Patent: Nov. 24, 2026

(54) TISSUE STIMULATORS AND CONNECTORS FOR USE WITH SAME

(71) Applicant: The Alfred E. Mann Foundation for Scientific Research, Valencia, CA (US)

(72) Inventors: William Andrew Brandt, Castaic, CA (US); Christopher Reed Jenney, Valencia, CA (US)

(73) Assignee: The Alfred E. Mann Foundation for Scientific Research, Valencia, CA (US)

( * ) Notice: Subject to any disclaimer, the term of this patent is extended or adjusted under 35 U.S.C. 154(b) by 331 days.

(21) Appl. No.: 18/439,009

(22) Filed: Feb. 12, 2024

(65) Prior Publication Data

US 2024/0316354 A1 Sep. 26, 2024

Related U.S. Application Data

(60) Provisional application No. 63/491,288, filed on Mar. 20, 2023.

(51) Int. Cl.
*A61N 1/37* (2006.01)
*A61N 1/05* (2006.01)
*A61N 1/375* (2006.01)

(52) U.S. Cl.
CPC ......... *A61N 1/3754* (2013.01); *A61N 1/0556* (2013.01)

(58) Field of Classification Search
CPC ... A61N 1/3754; A61N 1/0556; A61N 1/3752
See application file for complete search history.

(56) References Cited

U.S. PATENT DOCUMENTS

| | | | | |
|---|---|---|---|---|
| 5,082,453 | A | 1/1992 | Stutz, Jr. | |
| 5,906,634 | A * | 5/1999 | Flynn | A61N 1/3752 607/37 |
| 6,006,135 | A | 12/1999 | Kast et al. | |
| 6,741,892 | B1 | 5/2004 | Meadows et al. | |
| 7,630,768 | B1 * | 12/2009 | Coffed | A61N 1/3752 607/37 |
| 9,403,022 | B2 | 8/2016 | Ries et al. | |
| 9,956,394 | B2 | 5/2018 | Howard et al. | |
| 10,376,688 | B2 | 8/2019 | Chen et al. | |
| 2010/0160991 | A1 * | 6/2010 | Lim | A61N 1/3754 607/9 |
| 2015/0209575 | A1 * | 7/2015 | Black | A61N 1/0558 607/116 |
| 2018/0318577 | A1 | 11/2018 | Ng et al. | |
| 2018/0318578 | A1 | 11/2018 | Ng et al. | |
| 2019/0060646 | A1 | 2/2019 | Ng et al. | |
| 2019/0282805 | A1 | 9/2019 | Schmidt et al. | |
| 2022/0313987 | A1 | 10/2022 | Jenny et al. | |
| 2023/0010510 | A1 | 1/2023 | Brandt et al. | |

* cited by examiner

*Primary Examiner* — Rex R Holmes
(74) *Attorney, Agent, or Firm* — Henricks Slavin LLP

(57) ABSTRACT

An implantable pulse generator includes an electronics housing including an electronics container, stimulation circuitry within the housing, a plurality of feedthrough pins, operably connected to the stimulation circuitry, that extend in through the cover, an electrical connector including a plurality of pin receptacles and a plurality of conductive members respectively located within the pin receptacles, and a plurality of flexible wires that respectively connect one of the conductive members to one of the feedthrough pins.

20 Claims, 8 Drawing Sheets

TISSUE STIMULATORS AND CONNECTORS FOR USE WITH SAME

CROSS-REFERENCE TO RELATED APPLICATION

This application claims the benefit of U.S. Provisional Application No. 63/491,288, filed Mar. 20, 2023, and entitled "Tissue Stimulators And Connectors For Use With Same," which is incorporated herein by reference.

BACKGROUND OF THE INVENTIONS

1. Field of Inventions

The present inventions relate generally to implantable medical devices such as, for example, implantable tissue stimulators.

2. DESCRIPTION OF THE RELATED ART

Implantable tissue stimulators, which may include an implantable pulse generator ("IPG") and an electrode lead, are used to treat a wide variety of medical conditions. One such condition is obstructive sleep apnea (OSA), which is a highly prevalent sleep disorder that is caused by the collapse of or increase in the resistance of the pharyngeal airway, often resulting from tongue obstruction. Here, nerve fascicles of the hypoglossal nerve (HGN) that innervate the intrinsic and extrinsic muscles of the tongue are stimulated in a manner that prevents retraction of the tongue, which would otherwise close the upper airway during the inspiration portion of the respiratory cycle. Other exemplary medical conditions that may be treated with tissue stimulations include, but are not limited to, chronic pain syndrome, which may be treated spinal cord stimulation, neurological disorders, which may be treated with deep brain stimulation, and slow or irregular heartbeats, which may be treated with a pacemaker.

With respect to the tissue stimulators themselves, the IPGs may include a hermetically sealed electronics housing and a header with an electrical connector that is mounted on electronics housing. The IPG connector is connected to the electronics within the housing by way of feedthrough pins that extend through the housing. The electrode lead has an electrical connector that is configured to mate with IPG electrical connector.

SUMMARY

The present inventors have determined that implantable tissue stimulators are susceptible to improvement. In particular, the present inventors have determined that IPG and lead connectors, and the associated relationship between the IPG connectors and feedthrough pins, is susceptible to improvement. For example, many conventional IPG lead connectors include linearly spaced contact rings and pairs of seals associated with each contact ring, and lead connector includes a corresponding plurality of contact rings. The present inventors have determined that it would be desirable to employ connectors with circumferentially spaced pins (or sockets), instead of connectors with linearly spaced contacts, in IPG connectors to reduce cost and save space. With respect to circumferentially spaced pins, the use of circumferentially spaced feedthrough pins and a lead connector with pin receptacles that connect directly to the feedthrough pins has been proposed. The present inventors have determined that the use of feedthrough pins in this manner is undesirable because the orientation of connector formed from the feedthrough pins and/or arrangement of the pins within the connector are limited to the direction that the feedthrough pins pass through the IPG electronics housing and the arrangement thereof, whereas other orientations and arrangements may be better suited to a particular IPG and its intended application.

An implantable pulse generator in accordance with at least one of the present inventions includes an electronics housing including an electronics container, stimulation circuitry within the housing, a plurality of feedthrough pins, operably connected to the stimulation circuitry, that extend through the cover, an electrical connector including a plurality of pin receptacles, configured to receive the lead pins of an electrode lead connector, and a plurality of conductive members respectively located within the pin receptacles, and a plurality of flexible wires that respectively connect one of the conductive members to one of the feedthrough pins. The present inventions also includes tissue stimulators with such an implantable pulse generator and an electrode lead.

An implantable pulse generator in accordance with at least one of the present inventions includes an electronics housing including an electronics container, stimulation circuitry within the housing, a plurality of feedthrough pins, operably connected to the stimulation circuitry, that extend through the cover, an electrical connector including a plurality of connector pins, and a plurality of flexible wires that respectively connect one of the connector pins to one of the feedthrough pins. The present inventions also includes a tissue stimulator such an implantable pulse generator and an electrode lead.

There are a number of advantages associated with such implantable pulse generators and tissue stimulators. By way of example, but not limitation, the orientation and/or location of connector sockets (or pins) is not limited to the direction that the feedthrough pins pass through the IPG electronics housing.

BRIEF DESCRIPTION OF THE DRAWINGS

Detailed descriptions of exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions. For example, although described in the exemplary context of sleep apnea treatment, the present inventions are not so limited and are applicable to implantable tissue stimulators that are configured to treat other medical conditions.

Figure 1:
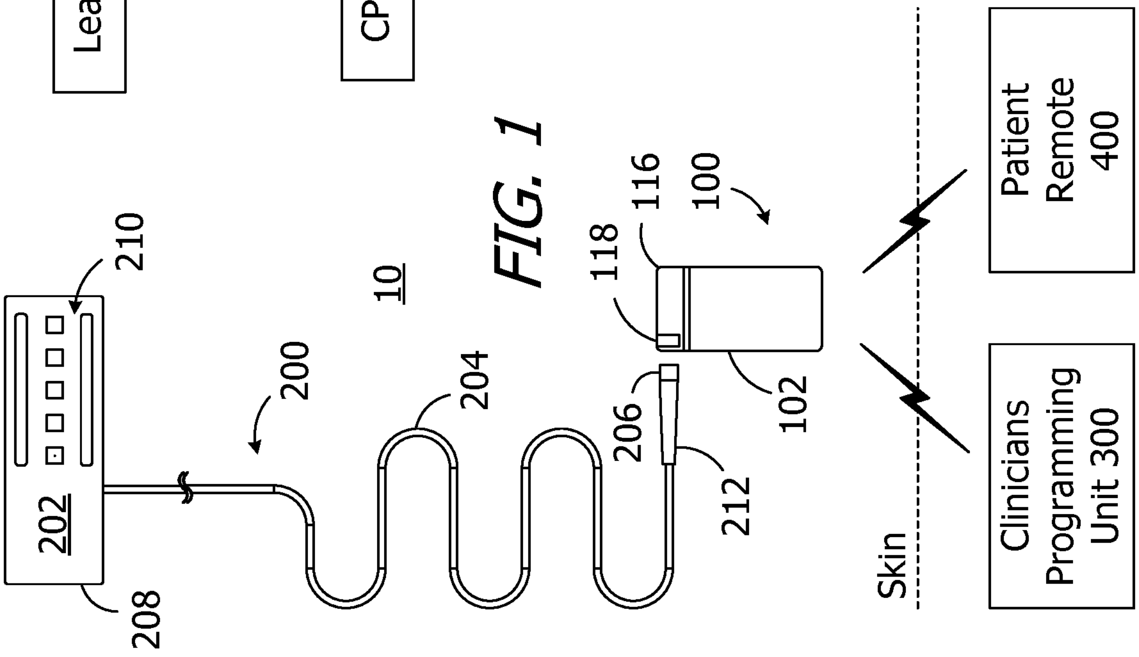
FIG. 1 is a plan view of a stimulation system in accordance with one embodiment of a present invention.
Figure 2:
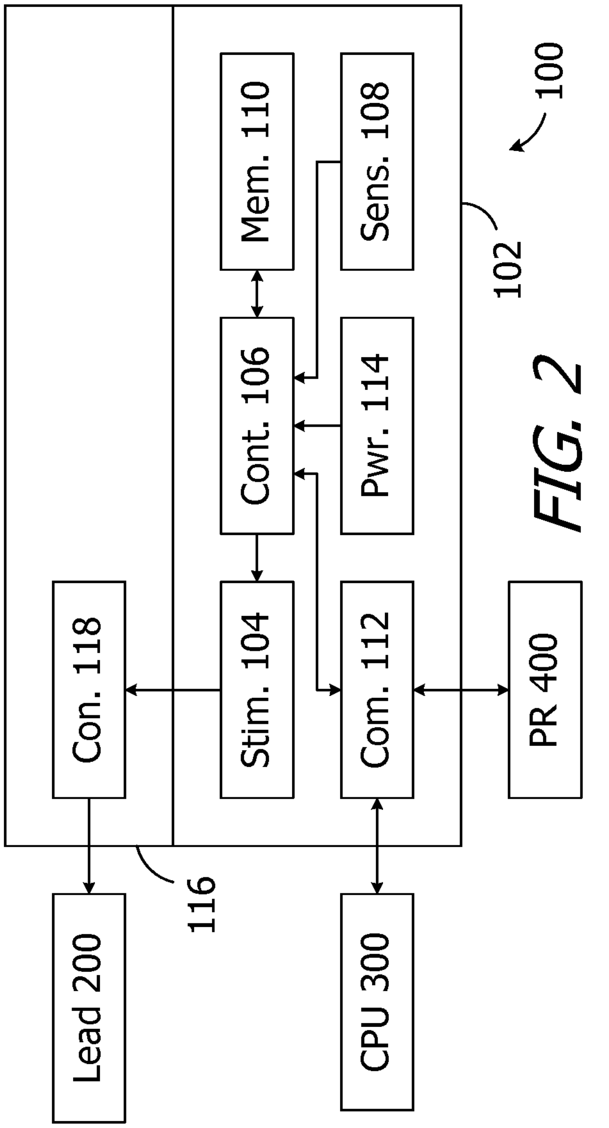
FIG. 2 is a block diagram of the stimulation system illustrated in FIG. 1.
Figure 3:
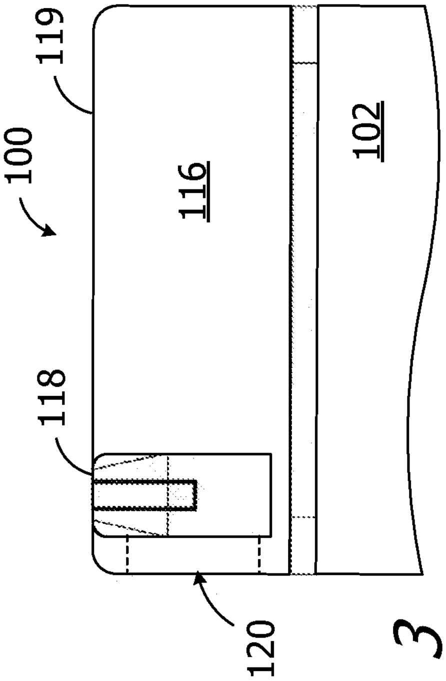
FIG. 3 is a side view of a portion of the IPG illustrated in FIG. 1.
Figure 5:
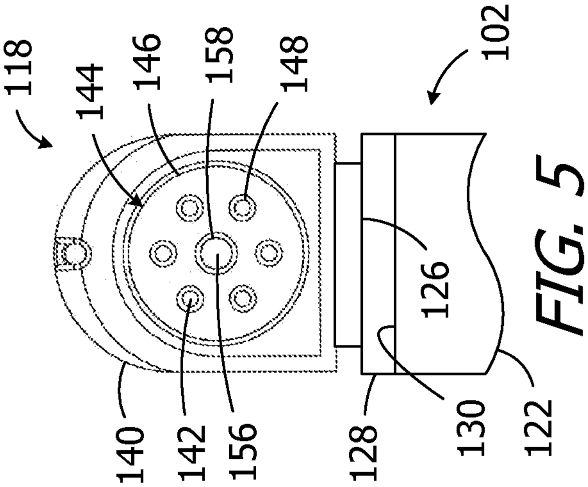
FIG. 5 is an end view of a portion of the IPG illustrated in FIG. 1.
Figure 7:
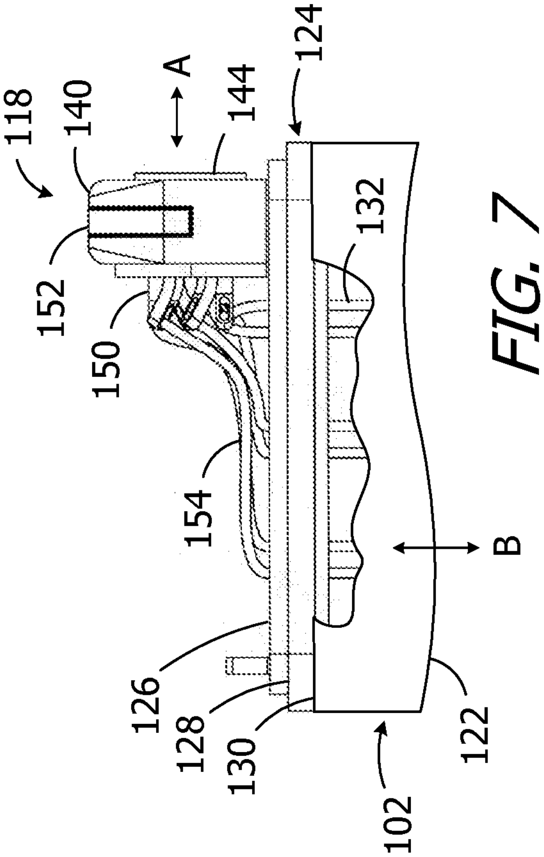
FIG. 7 is a side, cutaway view of a portion of the IPG illustrated in FIG. 1.
Figure 4:
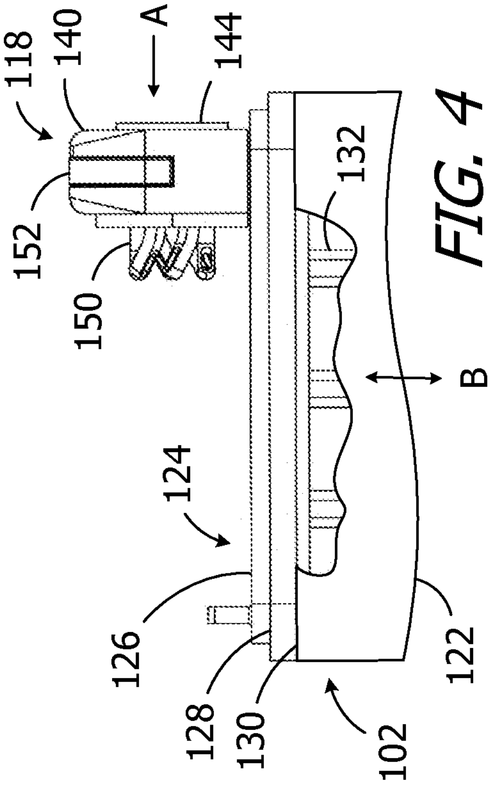
FIG. 4 is a side, cutaway view of a portion of the IPG illustrated in FIG. 1.
Figure 6:
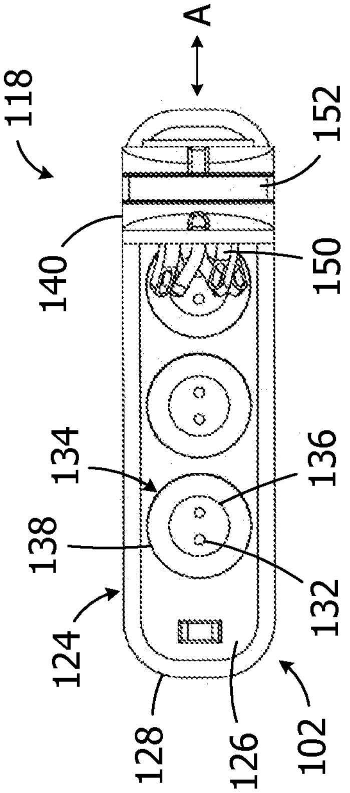
FIG. 6 is a top view of a portion of the IPG illustrated in FIG. 1.

Referring to FIGS. 1-3, an implantable tissue stimulator 10 in accordance with one embodiment of a present invention includes an implantable stimulator such as the implantable pulse generator ("IPG") 100 and an electrode lead 200. The implantable tissue stimulator 10 may be combined with a clinician's programming unit 300, a patient remote 400 and/or an IPG charger (not shown) in some instances.

The exemplary IPG 100 includes a hermetically sealed electronics housing 102 in which various circuitry (e.g., stimulation circuitry 104, control circuitry 106, sensing circuitry 108, memory 110 and communication circuitry 112) and a power supply 114 is located. The exemplary IPG 100 also includes a header assembly 116 that is secured to the electronics housing 102 and that may be composed of an IPG electrical connector 118 (or "IPG connector") and a polymer header body 119, such as a molded plastic or cast epoxy header body, that mounts the IPG connector to the exterior of the electronics housing. The IPG connector 118 is connected to the stimulation circuitry 104 by way of feedthrough pins and wires (discussed below with reference to FIGS. 4-7), and header assembly 116 includes a receptacle 120 to provide access to the IPG connector.

Figure 2A:
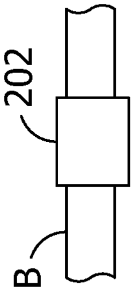
FIG. 2A is a plan view showing the nerve cuff illustrated in FIG. 1 on an HGN GM branch.

The exemplary electrode lead 200 illustrated in FIG. 1 includes a nerve cuff 202 and a lead body 204 that couples the nerve cuff 202 to the IPG 100 by way of a lead electrical connector (or "lead connector") 206 on the proximal end of the lead body 204. The exemplary nerve cuff 202 is configured in such a manner that it may be circumferentially disposed around, and provide stimulation energy to, either the HGN trunk or a HGN branch (e.g., the HGN GM branch B shown in FIG. 2A). The nerve cuff 202, which is shown in a unfurled state in FIG. 2 and is pre-set to a furled state, includes a cuff body 208 and a plurality of electrically conductive contacts (or "contacts") 210. A strain relief 212 is located adjacent to the lead connector 206. The lead body 204 in the illustrated implementation includes a plurality of S-shaped sections in order to provide strain relief and accommodate body movement at the location within the neck where the lead body 204 is implanted, thereby reducing the likelihood that damage to HGN, as well as fatigue damage of the lead body 204, that may result from neck movements. The lead body may also be straight in other implementations. The cuff body 208 in the exemplary implementation has a stimulation region with the contacts 210 and a compression region with no contacts. The compression region wraps around at least a portion of the stimulation region when the nerve cuff 102 is in the pre-shaped furled state, as well as in slightly larger, expanded and less tightly furled states, thereby improving the electrical connection between the contacts 210 and the nerve. Suitable cuff body materials may be biologically compatible, electrically insulative and elastic and include, but are not limited to silicone, polyurethane and styrene-isobutylene-styrene (SIBS) elastomers. The contacts 112 may differ in size and shape (as shown) or may be the same size and/or shape. Suitable contact materials includes, but are not limited to, platinum-iridium and palladium. The present electrode leads may include other types of nerve cuffs, such as helical and axial nerve cuffs, and various specific examples of nerve cuffs are illustrated and described in U.S. Pat. Pub. Nos. 2018/0318577A1, 2018/0318578A1, 2019/0060646A1, 2019/0282805A1, 2022/0313987A1 and 2023/10510A1, which are incorporated herein by reference in their entirety. The electrode leads of the present tissue stimulators may also include nerve paddles and nerve strips in place of the nerve cuffs.

In the exemplary context of OSA treatment, the circuitry within the electronics housing 102 housing may be configured to, for example, deliver stimulation energy to the HGN by way of the nerve cuff 202. Here, the control circuitry 106 may apply stimulation energy to either the HGN trunk or an HGN branch (e.g. the HGN GM branch) in various stimulation methodologies by way of the cuff 102 when the patient is in the inspiratory phase of respiration, and other conditions for stimulation are met, thereby causing anterior displacement of the longue to keep the upper airway unobstructed. The control circuitry 106 causes the stimulation circuitry 104 to apply stimulation in the form of a train of stimulation pulses during these inspiratory phases of the respiratory cycle (or slightly before the inspiration and ending at the end of inspiration) and not the remainder of the respiration cycle. The train of stimulus pulses may be set to a constant time duration or may change dynamically based on a predictive algorithm that determines the duration of the inspiratory phase of the respiratory cycle.

The sensing circuitry 108 may be connected to one or more sensors (not shown) that are contained within the housing 102. Alternatively, or in addition, the sensors may be affixed to the exterior of the housing 102 or positioned at a remote site within the body and coupled to the IPG 100 with a connecting lead. The sensing circuitry 108 can detect physiological artifacts that are caused by respiration (e.g., motion or ribcage movement), which are proxies for respiratory phases, such as inspiration and expiration or, if no movement occurs, to indicate when breathing stops. Suitable sensors include, but are not limited to, inertial sensors, bioimpedance sensors, pressure sensors, gyroscopes, ECG electrodes, temperature sensors, GPS sensors, and combinations thereof. The memory 110 stores data gathered by the sensing circuitry 108, programming instructions and stimulation parameters. The control circuitry 106 analyzes the sensed data to determine when stimulation should be delivered. The communication circuitry 112 is configured to wirelessly communicates with the clinician's programming unit 300 and patient remote 400 using radio frequency signals.

It should also be noted that although the exemplary tissue stimulator 10 illustrated in FIGS. 1-3 includes a single lead, the present inventions are not so limited. Other embodiments may, for example, include a pair of electrode leads 200 for bilateral HGN stimulation and an IPG (not shown) with two IPG connectors 118 and receptacles 120.

Turning to FIGS. 4-7, the exemplary hermetically sealed electronics housing 102 includes an electronics container 122 as well as a cover 124 with a central portion 126 and a flange 128 that extends outwardly from the central portion. The flange 128 rests on and is welded or otherwise bonded to the container rim 130 to form the sealed housing 102. Suitable materials for the container 122 and cover 124 include, but are not limited to, an electrically conductive, biocompatible material such as titanium. The stimulation circuitry 104 within the electronics housing 102 may be connected to components outside the housing by way of feedthrough pins 132 that extend through the cover central portion 126. In the illustrated embodiment, the feedthrough pins 132 are part of feedthrough assemblies 134 that each include a pair of feedthrough pins 132, a ceramic insulator 136 through which the feedthrough pins extend, and a base member 138 in which the ceramic insulator is mounted. The feedthrough assemblies 134 extend through apertures in the cover central portion 126 and are welded or otherwise bonded thereto.

The exemplary IPG connector 118, which is discussed in greater detail below with reference to FIGS. 8-13, includes a main body 140 with a plurality of circumferentially spaced pin receptacles 142, a seal 144 having a disk 146 and a plurality of apertures 148 extending through the disk that are respectively aligned with the pin receptacles, a plurality of conductive members 150 located within the pin receptacles and which extend from the pin receptacles to points outside the main body, and a removable clip 152 that is used to secure the lead connector 206 to the IPG connector 118 in the manner described below with reference to FIGS. 18-19. Flexible wires 154 connect the feedthrough pins 132 to the conductive members 150. A receptacle 156 for a centering post 234 on the lead connector 206 may also be provided, and the seal 144 may be provided with a corresponding aperture 158.

It should be noted here that as shown in, for example, FIGS. 4-7, the exemplary IPG connector 118 allows the feedthrough pins 132 to be connected (by way of wires 154) to circumferentially spaced pin receptacles 142 that are not in-line with the feedthrough pins 132 and, therefore, to lead connector pins 228 (discussed below) that are not in-line with the feedthrough pins 132. In the illustrated embodiment, and although the present inventions are not so limited, the pin receptacles 142 extend in direction A while the feedthrough pins 132 extend in direction B, which is perpendicular to direction A. In other implementations, the angle between direction A and direction B may be other then perpendicular, e.g., 15° or 30° or 45° or 60° or 75°.

Figure 8:
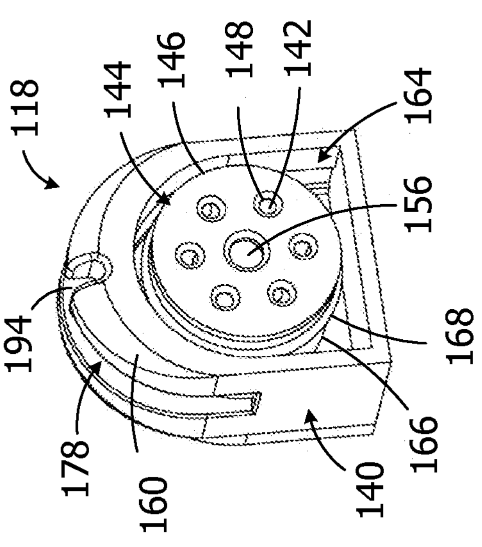
FIG. 8 is a perspective view of a portion of the IPG illustrated in FIG. 1.
Figure 9:
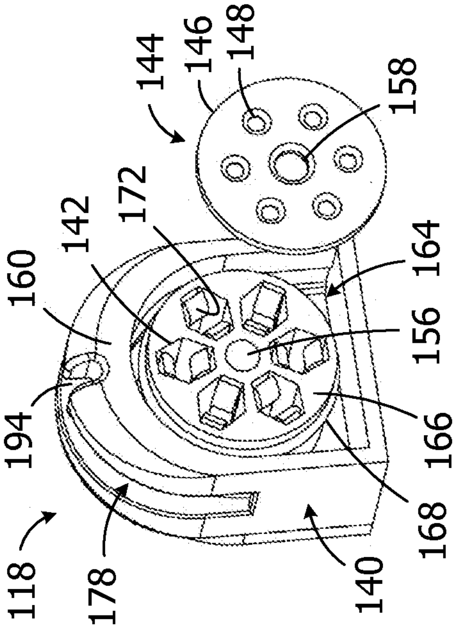
FIG. 9 is an exploded perspective view of a portion of the IPG illustrated in FIG. 1.

Turning to FIGS. 8 and 9, the main body 140 of the IPG connector 118 is configured to receive the lead connector 206 (described below with reference to FIGS. 14-17) and to create a seal between the IPG connector and the lead connector. To that end, the IPG connector main body 140 defines a front side 160, a rear side 162 and a recess 164 that extends inwardly from the front side. The recess 164 has a size and shape which corresponds to that of the lead connector main body 218. Although not limited to any particular shape, the main body recess 164 has an overall truncated obround shape in the illustrated embodiment and only allows for a single orientation when connecting to prevent clocking or misalignment. Proper orientation may also be achieved using pin positioning and other geometric features such as a rib and matching groove. A center post 166, with a size and shape that corresponds to that of the lead connector socket 224, is located within the recess 164. The pin receptacles 142 are defined by and extend through the center post 166, the seal 144 is located at a longitudinal end of the center post, and an o-ring seal 168 is mounted on the exterior of the center post between the longitudinal ends thereof. The seal 144 engages the lead connector pins 228 and may in some instances engage center post 234, while the seal 168 engages the surface 225, as is discussed below with reference to FIG. 20. The seals 144 and 168 and the engagement thereof prevent fluid ingress into the pin receptacles 142 and lead connector socket 224. Suitable materials for the main body 140 include, but are not limited to, polysulfone, Ultem® polyetherimide and polyether ether ketone (PEEK), while suitable materials for the seals 144 include, but are not limited to, silicone.

Figure 10:
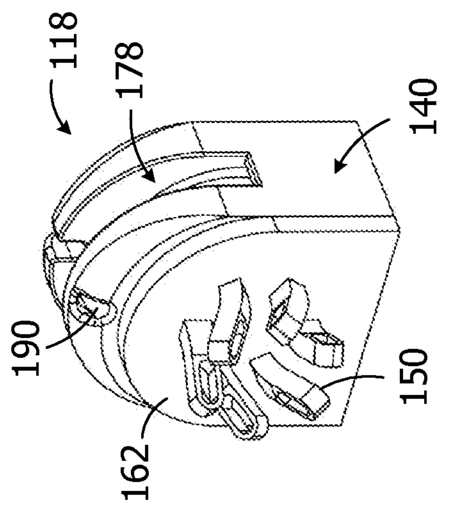
FIG. 10 is a perspective view of a portion of the IPG illustrated in FIG. 1.
Figure 11:
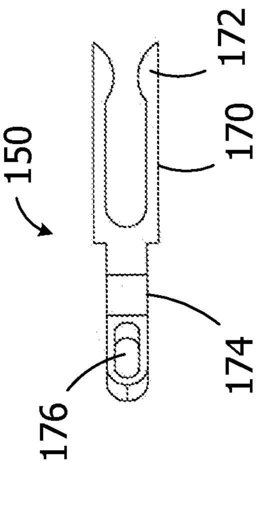
FIG. 11 is a plan view of a portion of the IPG illustrated in FIG. 1.
Figure 12:
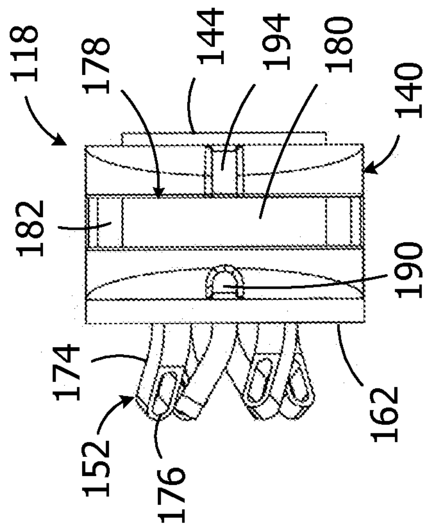
FIG. 12 is a top view of a portion of the IPG illustrated in FIG. 1.
Figure 13:
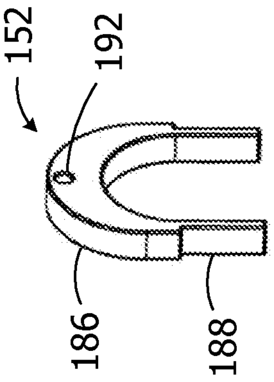
FIG. 13 is a perspective view of a portion of the IPG illustrated in FIG. 1.
Figure 14:
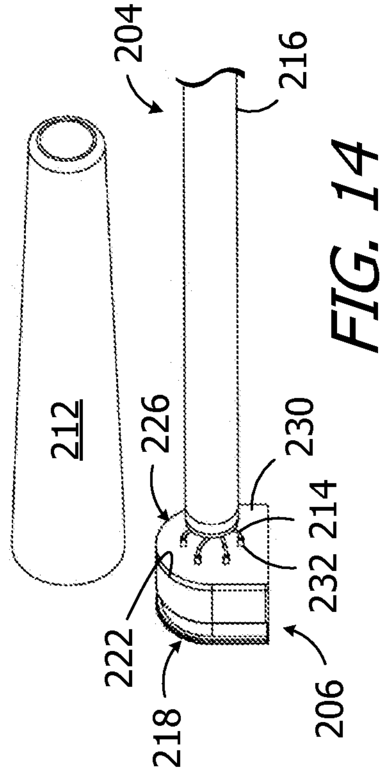
FIG. 14 is an exploded perspective view of a portion of the lead illustrated in FIG. 1.
Figure 15:
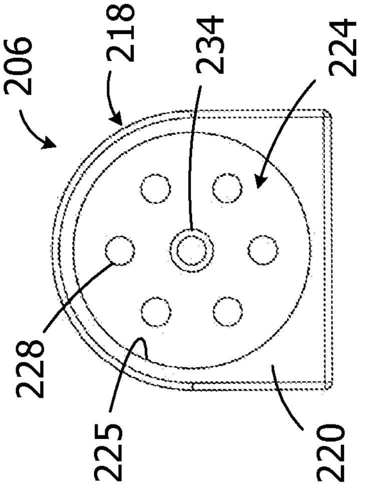
FIG. 15 is an end view of a portion of the lead illustrated in FIG. 1.
Figure 16:
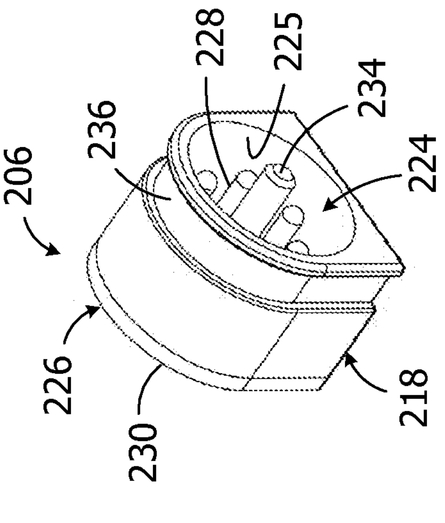
FIG. 16 is a perspective view of a portion of the lead illustrated in FIG. 1.
Figure 17:
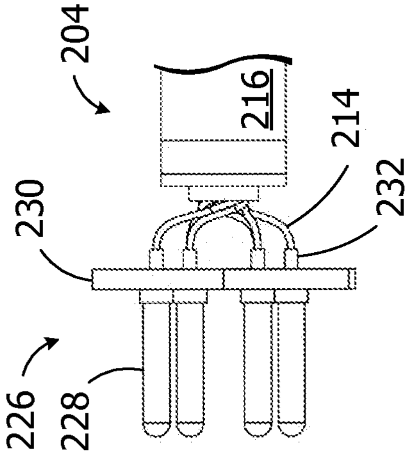
FIG. 17 is a side view of a portion of the lead illustrated in FIG. 1.

Turning to FIGS. 9-11, the conductive members 150 in the exemplary embodiment may include a pair of arms 170, with inwardly extending contact surfaces 172, and a post 174 with a wire aperture 176. The distance between the contact surfaces 176 is slightly less than the diameter of the lead pins 228 so that the arms 170 will spread slightly and resiliently maintain contact between the contact surfaces and the pins. The arms 170 also prevent the conductive members 150 from being pushed through the main body 140. The posts 174 extend through the rear side 162 of the main body 140. The posts 174 may also be bent and oriented in the manner shown to prevent the conductive members 150 from being pulled from the main body 140 and to facilitate placement of the ends of the wires 154 into the wire apertures 176, where they are soldered in place. Suitable electrically conductive materials for the conductive members 150 include, but are not limited to MP35N® nickel-cobalt base alloy.

The lead connector 206 may also be locked to the IPG connector 118 in any suitable manner. By way of example, but not limitation, the exemplary tissue stimulator 10 employs the slot and clip arrangement illustrated in FIGS. 12 and 13. The IPG connector main body 140 has a U-shaped slot 178 with a central portion 180 and a pair of thin side portions 182, while the clip 152 has a central portion 186 and a pair of thin side portions 188. The lead connector recess 236 (FIG. 16) will be aligned with the slot 178 when the lead connector 206 is fully inserted IPG connector 118. When the clip 152 is inserted into the slot 178, a portion of the clip 152 will about the IPG connector main body 140 and a portion of the clip will be located within the lead connector recess 236, thereby preventing separation of the lead connector 206 from the IPG connector 118 in the manner described below with reference to FIGS. 18-19. The IPG connector main body 140 and clip 152 may also include corresponding suture apertures 190 and 192 through which a suture may be passed and then knotted to prevent removal of the clip. The connector main body 140 may also include a slot 194 to facilitate this process as well as removal of the clip during disassembly.

Referring now to FIGS. 14-17, the exemplary lead body 204 includes a plurality of wires or cables 214 and an outer tube 216 through which the wires pass. The exemplary lead connector 206 includes a main body 218 with a front side 220, a rear side 222 and a post receptacle 224 that is sized and shaped to receive the IPG connector center post 166 (FIGS. 8 and 9), and a pin assembly 226 with a plurality of electrically conductive pins (or "pins") 228 that are carried by a non-conductive pin support 230. The pins 228 extend through rear side apertures (not shown) and into the post receptacle 224, and the pin support 230 is secured to the main body rear side 222. One end of each wire 214 is connected to a respective pin 228 by way of crimp tubes 232 that extend through the pin support 230. The other end of each wire 214 is connected to a respective contact 210 on the nerve cuff 202 (FIG. 1). A central post 234 that is configured to be received by the IPG connector receptacle 156, to center the lead connector 206 relative to the IPG connector 118, may also be provided within the receptacle 224. The outer surface of the main body 218 has a shape corresponding to that of the IPG connector recess 164 (i.e., a truncated obround shape in the illustrated embodiment) and also includes a recess 236 that is configured to receive the clip 152.

Figure 19:
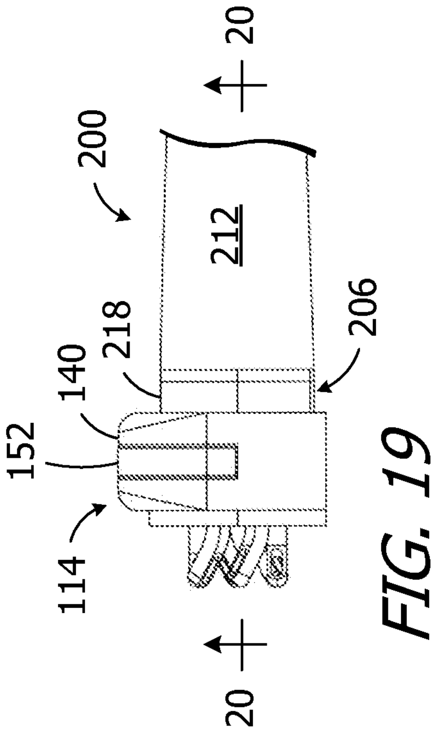
FIG. 19 is a side view of portions of the IPG and lead illustrated in FIG. 1 in a connected state.
Figure 20:
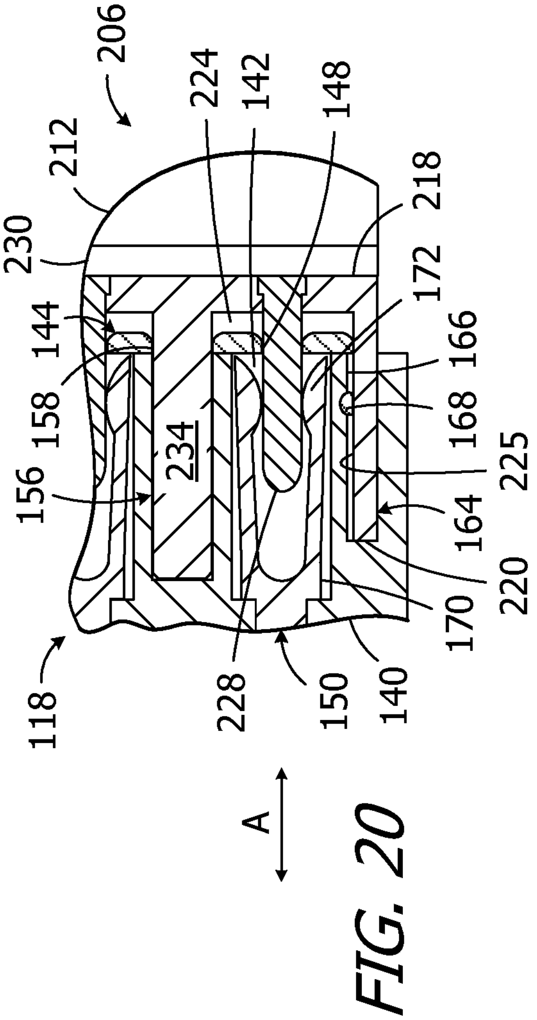
FIG. 20 is a partial section view taken along line 20-20 in FIG. 19.
Figure 18:
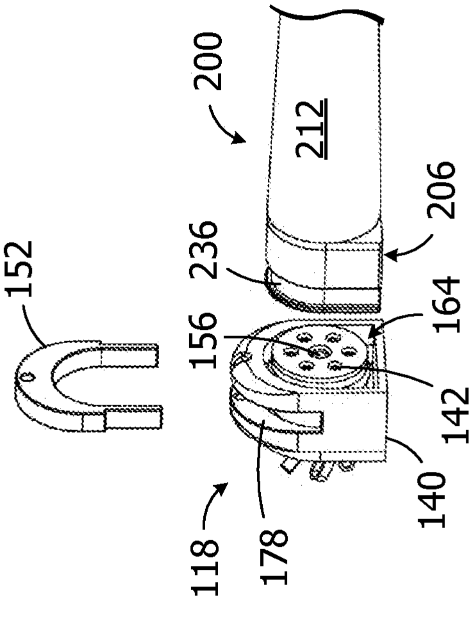
FIG. 18 is a perspective view of portions of the IPG and lead illustrated in FIG. 1 in a disconnected state.

The exemplary lead connector 206 may be connected to the IPG connector 114 in in the manner illustrated in FIGS. 18-20. With the clip 152 removed from the slot 178, the lead connector main body 218 may be aligned with the IPG connector main body recess 164, as shown in FIG. 18. Such alignment also aligns the lead connector pins 228 with the pin receptacles 142 and the central post 234 with the receptacle 156. The aligned lead connector 206 may then be pushed into the connector 114 until the lead connector is fully inserted, where the main body front side 220 abuts the closed end of the main body recess 164 and the central post 234 abuts the closed end of the receptacle 156. During the insertion, the lead connectors pins 228 will engage the contact surfaces 172 of the conductive members 150, thereby resiliently spreading the arms 170 so that contact is maintained between the contact surfaces 172 and the lead connector pins 228. In addition, the lead connector pins 228 and the central post 234 will be engaged by the seal 144 on the end of the center post 166 as the connector pins and central post pass through the apertures 148 and 158 that extend through the seal disk 146. The o-ring seal 168 will be compressed between the center post 166 and the inner surface 225 of the lead connector main body 218. Full insertion of the lead connector 206 into the IPG connector 114 will also result in alignment of the main body recess 236 of the lead connector with the main body slot 178 of the IPG connector, thereby facilitating placement of the clip 152 into the recess and the slot to prevent the lead 200 from being disconnected from the IPG 100.

Figure 22:
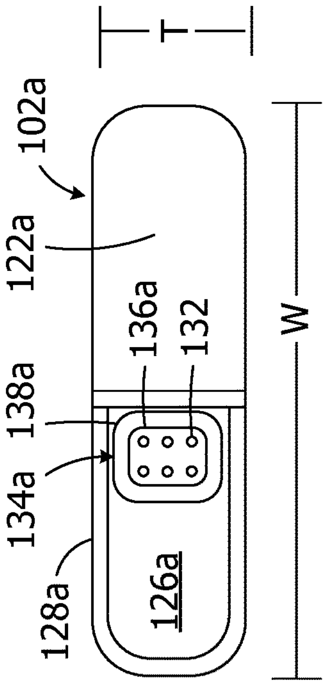
FIG. 22 is a top view of a portion of the IPG illustrated in FIG. 21.
Figure 21:
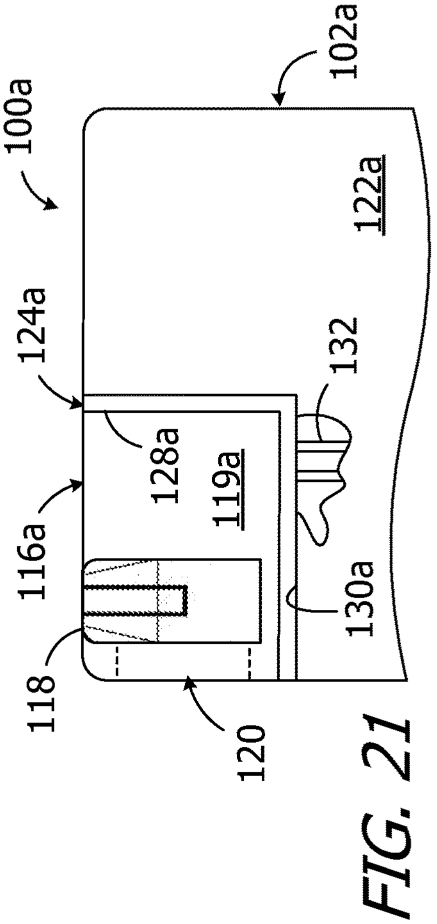
FIG. 21 is a side, cutaway view of a portion of an IPG in accordance with one embodiment of a present invention.
Figure 23:
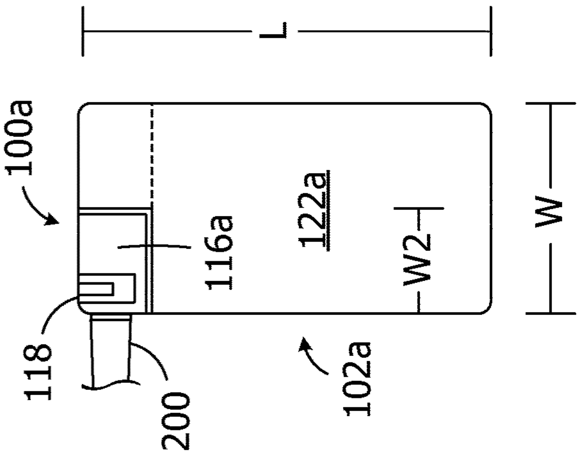
FIG. 23 is a side view of the IPG illustrated in FIG. 21 and a portion of a lead.
Figure 26:
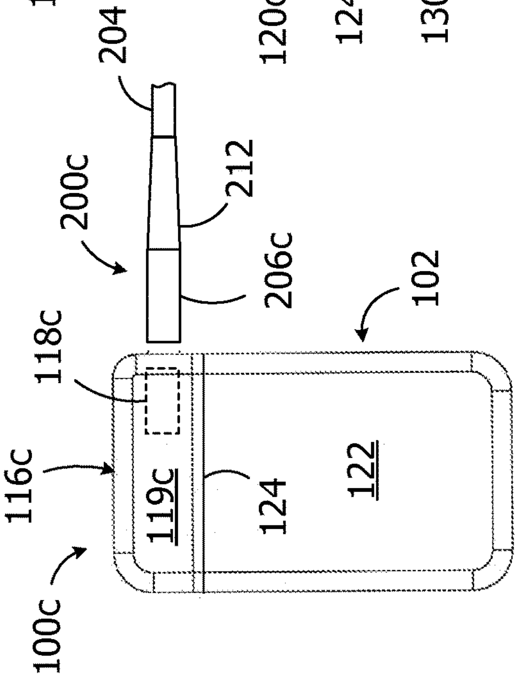
FIG. 26 is an exploded side view of an IPG and a lead in accordance with one embodiment of a present invention.
Figure 27:
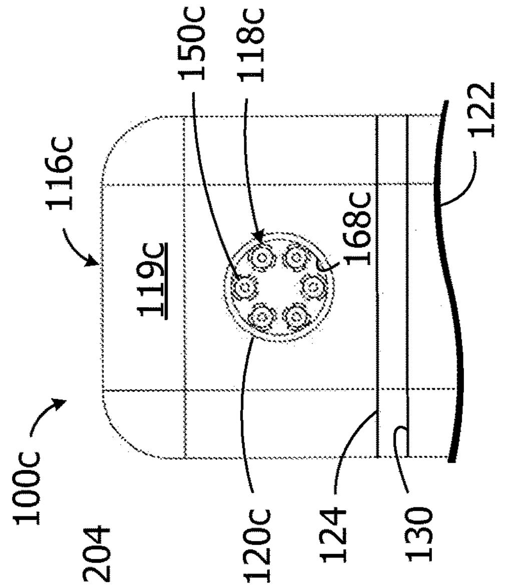
FIG. 27 is an end view of a portion of the IPG illustrated in FIG. 26.

Referring to FIGS. 21-23, another exemplary IPG is generally represented by reference numeral **100*a*. The IPG 100*a* is essentially identical to IPG 100 and similar elements are represented by similar reference numbers. For example, the exemplary IPG 100*a* includes a hermetically sealed electronics housing 102*a* in which various circuitry is located (such as that described above) and a header assembly 116*a* with an IPG connector 118. Here, however, the feedthrough pins 132 are all located relatively close to the IPG connector, which allows the overall volume of the IPG to be used more efficiently. In particular, the IPG 100*a* defines a length L, a width W less than the length and a thickness T less than the width. The width of the header assembly 116*a*, which includes the IPG connector 118 and a polymer header body 119*a* that mounts the IPG connector to the exterior of the electronics housing, is less than the overall width of the IPG. In the illustrated embodiment, the width W2 is about 50% of the overall width W of the IPG 100*a*. To that end, the electronics container 122*a* includes a portion that extends the entire length L of the IPG 100*a*, a portion that extends less than the entire length of the IPG 100*a*, and a container rim 130*a* with a portion that extends in the length direction and a perpendicular portion that extends in the width W direction. A cover 124*a*, with a central portion 126*a* and a flange 128*a* that extends outwardly from the central portion, rests on and is welded (or otherwise bonded) to the container rim 130*a*. The cover 124*a* has a shape corresponding to that of the container rim 130*a* and includes a portion that extends in the length L direction and a perpendicular portion that extends in the width W direction. All of the feedthrough pins 132 (six in the illustrated embodiment) are part of the same feedthrough assembly 134*a* that includes a ceramic insulator 136*a* through which the feedthrough pins extend and a base member 138*a* in which the ceramic insulator is mounted. The feedthrough assembly 134*a* extends through an aperture in the cover central portion 126*a* and is welded (or otherwise bonded) to the electronics container 122*a*. The feedthrough pins 132 may be connected to the IPG connector 118** by wires (not shown) in the manner described above.

Figure 25:
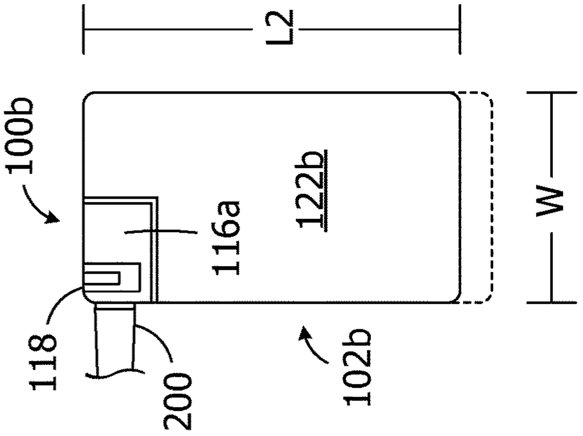
FIG. 25 is a side view of an IPG and a portion of a lead in accordance with one embodiment of a present invention.
Figure 24:
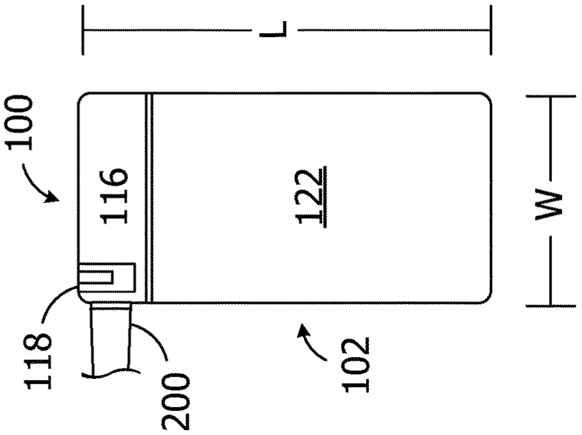
FIG. 24 is a side view of the IPG illustrated in FIG. 1 and a portion of a lead.

The volumetric efficiency provided by header assembly **116*a* is illustrated in FIGS. 23-25. The electronics container 122*a* of the IPG 100*a* illustrated in FIG. 23 is larger than the electronics container 122 of the otherwise identical IPG 100 illustrated in FIG. 24, despite the fact that the overall size (as defined by the length L, width W and thickness T) is the same. The additional volume of the electronics container 122*a*, as compared to the electronics container 122, is the volume above the dashed line in FIG. 23. The volumetric efficiency provided by header assembly 116*a* may also be used to increase the volume available for internal components or to reduce overall IPG size. For example, the IPG 100*b* illustrated in FIG. 25 is essentially identical to the IPG 100*a* and similar elements are represented by similar reference numerals. Here, however, the electronics container 112*b* of the housing 102*b* has a length L2 that is less than that of the IPG 100 illustrated in FIG. 24. The reduction in length (as shown with the dashed line in FIG. 25) results in the electronics container 122***b* having the same volume as the electronics container 122 despite the reduction in length and the resulting overall reduction in IPG size.

Turning to FIGS. 26-30, another exemplary IPG is generally represented by reference numeral 100*c*. The IPG 100*c* is essentially identical to IPG 100 and similar elements are represented by similar reference numbers. For example, the exemplary IPG 100*c* includes a hermetically sealed electronics housing 102 in which various circuitry is located (such as that described above) and the housing has an electronics container 122 and cover 124. A header assembly 116*c*, which is secured to the electronics housing 102, includes an IPG connector 118*c* and a polymer header body 119*c* that mounts the IPG connector to the exterior of the electronics housing. The IPG connector 118*c* is connected to the stimulation circuitry 104 (FIG. 2) by way of feedthrough pins and wires in the manner described above. A receptacle 120*c* provides access to the IPG connector 118*c* for the connector 2060 (described below with reference to FIGS. 31-34) of a lead 200*c* that is otherwise identical to lead 200.

Figure 28:
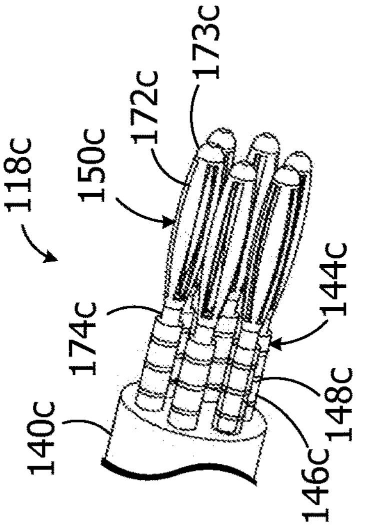
FIG. 28 is a perspective view of a portion of the IPG illustrated in FIG. 26.
Figure 29:
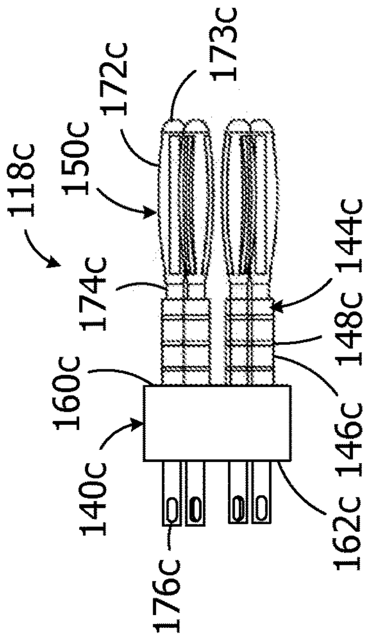
FIG. 29 is a side view of a portion of the IPG illustrated in FIG. 26.
Figure 30:
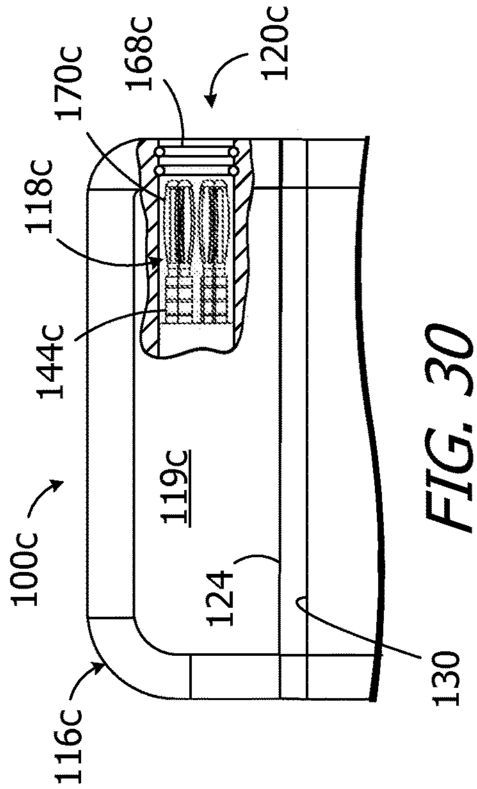
FIG. 30 is a side, cutaway view of a portion of the IPG illustrated in FIG. 26.
Figure 31:
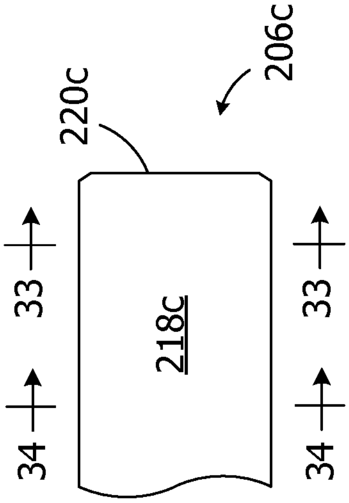
FIG. 31 is a side view of a portion of the lead illustrated in FIG. 26.
Figure 32:
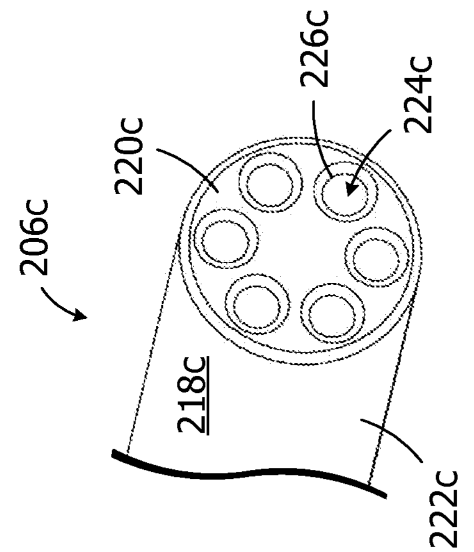
FIG. 32 is a perspective view of a portion of the lead illustrated in FIG. 26.
Figure 33:
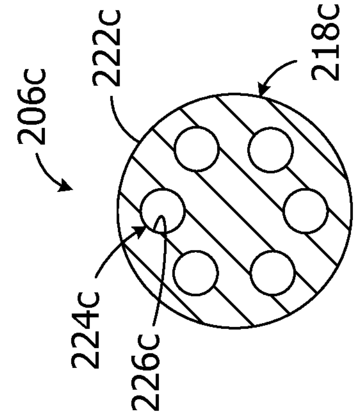
FIG. 33 is a section view taken along line 33-33 in FIG. 31.
Figure 34:
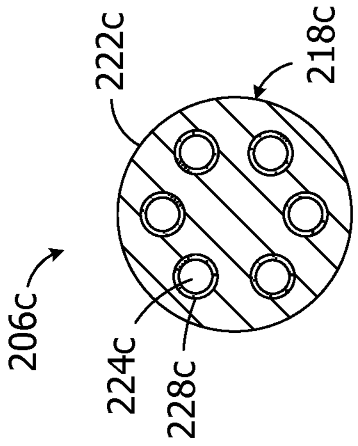
FIG. 34 is a section view taken along line 34-34 in FIG. 31.

Referring more specifically to FIGS. 28 and 29, the IPG connector 118*c* includes a main body 140*c*, with a front side 160*c* and a rear side 162*c*, and a plurality of circumferentially spaced compressible electrically conductive pins (or "compressible pins") 150*c*. Each compressible pin 150*c* includes a plurality of leaf springs 172*c* that extend from a tip 173*c* to a post 174*c*. The posts 174*c* extend through the main body 140*c* and include wire apertures 176*c*. The relative size of the leaf springs 172*c* and the lead connector 206*c* (discussed below with reference to FIGS. 31-34) are such that the leaf springs will be compressed when the lead connector 206*c* is inserted into the IPG connector 118*c*. There may also be a seal 144*c* associated with each of the compressible pins 150*c*. The exemplary seals 144*c*, which include a cylindrical portion 146*c* and a plurality of o-rings 148*c*, are engaged by the surfaces of the receptacles surfaces 226*c* (FIG. 33). Other seals may be associated with the receptacle 120*c*. In the illustrated embodiment, the receptacle includes a pair of o-rings 168*c* (FIG. 30) that engage the lead connector outer surface 222*c* (FIGS. 32-34) when the lead connector 206*c* is inserted into the IPG connector 118*c*.

The exemplary lead connector 206*c* illustrated in FIGS. 31-34, which is configured to mate with the above-described IPG connector 118*c*, includes a main body 218*c*, with a front side 220*c* and an outer surface 222*c*, and a plurality of receptacles 224*c* with surfaces 226*c*. Conductive tubes 228*c* are located within the receptacles and are inwardly spaced from the front side 220*c*. The conductive tubes 228*c* are connected to wires 214 (FIG. 14) that extend through the lead body 204 to the nerve cuff 202 (FIG. 1).

The lead connector 206*c* may be inserted into the IPG connector 118*c* until the front side 220*c* of the lead connector main body 218*c* is adjacent to the front 160*c* of the IPG connector main body 140*c*. The compressible pins 150*c* will pass through the receptacles 224*c* and into the conductive tubes 228*c*, where the leaf springs 172*c* will be compressed and electrical contact will be made. In some instances, mechanical features and/or main body shapes (not shown) may be provided to ensure the desired orientation of the lead connector 206*c* relative to the IPG connector 118*c*. Additionally, although the pins 150*c* and pin receptacles 224*c* described above are symmetrically spaced, they may be asymmetrically spaced in other implementations. With respect to fluidic sealing, the inner surfaces 226*c* of the lead connector receptacles 224*c* will engage the IPG connector seals 144*c*, while the outer surface 222*c* of the lead connector main body 218*c* engages the IPG connector seals 168*c*.

It should also be noted here that the connector 118*c* may be incorporated into IPGs similar to those described above with reference to FIGS. 21-23 and 25.

The connectors 118 and 118*c* may also be employed in conjunction with hermetically sealed electronics housings that do not include a cover. Here, the electronics container may be formed from two "clamshell" parts. A small opening with a rim remains after the two "clamshell" parts are welded together to form the electronics container. The opening may be closed, and sealed, feedthrough assembly (similar to feedthrough assembly 134*a*) that includes a feedthrough pins, a ceramic insulator through which the feedthrough pins extend, and a base member, in which the ceramic insulator is mounted, that may be placed on the rim and welded directly to the electronics container, thereby eliminating the need for a cover.

Although the inventions disclosed herein have been described in terms of the preferred embodiments above, numerous modifications and/or additions to the above-described preferred embodiments would be readily apparent to one skilled in the art. It is intended that the scope of the present inventions extend to all such modifications and/or additions. The inventions include any and all combinations of the elements from the various embodiments disclosed in the specification. The scope of the present inventions is limited solely by the claims set forth below.

We claim:

1. An implantable pulse generator for use with an electrode lead having a lead connector with lead pins, the implantable pulse generator comprising:
- an electronics housing including an electronics container;
- stimulation circuitry within the housing;
- a plurality of circumferentially spaced feedthrough pins, operably connected to the stimulation circuitry, that extend through the electronics housing;
- an electrical connector including a plurality of pin receptacles, configured to receive the lead pins and a plurality of conductive members respectively located within the pin receptacles; and
- a plurality of flexible wires that respectively connect one of the conductive members to one of the feedthrough pins.

2. The implantable pulse generator claimed in claim 1, wherein
- the feedthrough pins extend in a first direction and the pin receptacles extend in a second direction that is different than the first direction.

3. The implantable pulse generator claimed in claim 2, wherein
- the second direction is perpendicular to the first direction.

4. The implantable pulse generator claimed in claim 2, wherein
- the first and second direction define a non-zero angle therebetween.

5. The implantable pulse generator claimed in claim 1, wherein
- the electrical connector includes a recess and a center post that is located within the recess and that defines longitudinal ends and an outer surface between the longitudinal ends; and
- the pin receptacles are located within the center post.

6. The implantable pulse generator claimed in claim 5, further comprising:

a seal, located on a longitudinal end of the center post, including a disk and a plurality of apertures that extend through the disk and that are respectively aligned with the pin receptacles.

7. The implantable pulse generator claimed in claim 5, further comprising:

a seal located on the outer surface of the center post.

8. The implantable pulse generator claimed in claim 1, wherein the implantable pulse generator defines a length, a width that is less than the length, and a thickness that is less than the width;

the electrical connector and all of the feedthrough pins are part of a header assembly; and the header assembly and the electronics container each occupy a respective portion of the width along the same portion of the length.

9. The implantable pulse generator claimed in claim 8, wherein the header assembly and the electronics container each occupy about 50% of the width along the same portion of the length.

10. A tissue stimulator, comprising:

the implantable pulse generator claimed in claim 1; and an electrode lead including an elongate lead body having a proximal end and a distal end, a plurality of electrically conductive contacts associated with the distal end of the lead body, and a lead connector associated with proximal end of the lead body and having a plurality of pins configured to be received by the pin receptacles.

11. The tissue stimulator claimed in claim 10, wherein the electrode lead includes a nerve cuff and the electrically conductive contacts are part of the nerve cuff.

12. An implantable pulse generator, comprising:

an electronics housing including an electronics container;

stimulation circuitry within the electronics housing;

a plurality of feedthrough pins, operably connected to the stimulation circuitry, that extend through the electronics housing;

an electrical connector including a plurality of circumferentially spaced connector pins; and a plurality of flexible wires that respectively connect one of the connector pins to one of the feedthrough pins.

13. The implantable pulse generator claimed in claim 12, wherein the feedthrough pins extend in a first direction and the connector pins extend in a second direction that is different than the first direction.

14. The implantable pulse generator claimed in claim 13, wherein the second direction is perpendicular to the first direction.

15. The implantable pulse generator claimed in claim 13, wherein the first and second direction define a non-zero angle therebetween.

16. The implantable pulse generator claimed in claim 12, wherein the connector pins include a compressible portion and a post.

17. The implantable pulse generator claimed in claim 12, further comprising:

a plurality of seals respectively associated with the plurality of connector pins.

18. The implantable pulse generator claimed in claim 12, wherein:

the electrical connector and all of the feedthrough pins are part of a header assembly; and the header assembly includes a receptacle that provides access to the electrical connector and a seal within the receptacle.

19. A tissue stimulator, comprising:

the implantable pulse generator as claimed in claim 12; and an electrode lead including an elongate lead body having a proximal end and a distal end, a plurality of electrically conductive contacts associated with the distal end of the lead body, and a lead connector associated with proximal end of the lead body and having a plurality of pin receptacles and a plurality of conductive tubes located within the pin receptacles.

20. The tissue stimulator as claimed in claim 19, wherein the electrode lead includes a nerve cuff and the electrically conductive contacts are part of the nerve cuff.

* * * * *